United States Patent [19]

Namimatsu et al.

[11] Patent Number: 5,063,045

[45] Date of Patent: Nov. 5, 1991

[54] METHOD FOR EVALUATING ANTIALLERGIC SUBSTANCES

[75] Inventors: Akio Namimatsu; Kouichiro Go, both of Hyogo, Japan

[73] Assignee: Nippon Zoki Pharmaceutical Co., Ltd., Osaka, Japan

[21] Appl. No.: 506,039

[22] Filed: Apr. 9, 1990

[30] Foreign Application Priority Data

Apr. 10, 1989 [JP] Japan .................................. 1-91578

[51] Int. Cl.$^5$ ............................................. A61K 49/00
[52] U.S. Cl. ........................................ 424/9; 514/324; 514/826
[58] Field of Search ..................... 424/9; 514/324, 826

[56] References Cited

U.S. PATENT DOCUMENTS 4,416,892  11/1983  Dawson .......................... 514/849 X
4,906,658   3/1990  Williams et al. .................... 514/473

Primary Examiner—Leonard Schenkman
Attorney, Agent, or Firm—Armstrong, Nikaido, Marmelstein, Kubovcik & Murray

[57] ABSTRACT

Antiallergic substances, are evaluated by measuring the amount of nasal secretion quantitatively using experimental animal models with nasal mucosal hypersensitivity.

6 Claims, No Drawings

METHOD FOR EVALUATING ANTIALLERGIC SUBSTANCES

BACKGROUND OF THE INVENTION

The present invention relates to a method for evaluating antiallergic substances, characterized by measuring the amount of nasal secretion quantitatively, using experimental animal models with nasal mucosal hypersensitivity.

There are several methods for assaying nasal mucosal sensitivity when evaluating antiallergic substances, and one of these is an assay method based on the amount of nasal secretion. But when using small animals, such as rats and guinea pigs, it is difficult to make a quantitative assay of the amount of nasal secretion. Heretofore, a method of scoring based on a tester's subjective observation has been employed, but this method is not a quantitative assay in the strict sense of the word.

An object of the present invention is to provide a method for evaluating antiallergic substances, characterized by measuring the amount of nasal secretion quantitatively, using experimental animal models with nasal mucosal hypersensitivity.

DETAILED DESCRIPTION OF THE INVENTION

The present invention is a method for evaluating antiallergic substances, characterized by measuring the amount of nasal secretion quantitatively, using experimental animal models with nasal mucosal hypersensitivity.

It is possible to evaluate the efficacy of antiallergic substances more clearly by using experimental animal models with nasal mucosal hypersensitivity than by using normal animals. Animals loaded with stress by a change of environmental rhythm or animals with enhanced nasal mucosal sensitivity induced by repeated nasal provocations with an allergen in actively sensitized animals are preferred.

Stress by change of rhythm in environmental temperature (SART stress: Specific Alternation of Rhythm in environmental Temperature-stress) is loaded onto the animals by keeping experimental animals in a stressed condition intermittently at a low temperature (from $-3°$ C. to $8°$ C.) and at a normal temperature (from $20°$ C. to $25°$ C.). It is possible to load stress of various intensities by suitable manipulation of the environmental conditions of a low temperature and normal temperature and duration of the loading periods. The SART stressed animals can be obtained, for example, according to the method of Kita et al [Folia Pharmocol. Japon., 71, 195–210 (1975)].

In the SART stressed animals, abnormalities in vital functions, such as a gradual decline in body weight gain, a lowering of sensitivity to acetylcholine of isolated duodenum, an increase of respiration and heart rate, a prolongation of QRS time and the like, have been reported. Through pathological studies of the SART stressed animals, it has been found that SART stressed animals showed a significant increase in the amount of nasal secretion and nasal mucosal hypersensitivity by nasal provocation with allergen, after passive sensitization.

Animals with nasal mucosal hypersensitivity obtained by repeated nasal provocations with an allergen in actively sensitized animals can be employed as the experimental animal models with nasal mucosal hypersensitivity in the method of the present invention.

Active sensitization with an allergen can be carried out by conventional methods commonly employed in this field, for example, by giving an allergen, such as ovalbumin, DNP-ascaris or DNP-bovine serum albumin, if necessary with an adjuvant, to experimental animals more than at least three times, at suitable intervals from one week to one month.

Experimental animal models with nasal mucosal hypersensitivity can be obtained by repeated nasal provocations with the allergen in actively sensitized animals. The conventional methods for inducing nasal secretion, for example, administering allergen or a chemical mediator, such as histamine, methacholine or acetylcholine intranasally, can be employed as the method in the present invention for inducing nasal secretion in the experimental animal models with nasal mucosal hypersensitivity.

The method for preparing experimental animal models with nasal mucosal hypersensitivity by repeated nasal provocations with allergen in actively sensitized animals requires a long term of sensitization. But the procedures for obtaining sensitized animals are relatively simple, and animal models with nasal mucosal hypersensitivity have the advantage of being can be used repeatedly after intervals at which no test drug is administered.

The method of the present invention can provide a clear evaluation of the inhibitory action of drugs for nasal secretion, by using experimental animal models with nasal mucosal hypersensitivity, where the inhibitory action could not be measured using normal animals.

Common experimental animals, for example, rats, mice, guinea pigs, hamsters, rabbits, monkeys such as common tupia and the like, can be used as the animals employed in the method of the present invention for evaluating antiallergic substances. Guinea pigs and hamsters are preferred because they are readily available and because of the size and shape of their noses.

Consistent data can be obtained using animals with substantially equal nasal mucosal sensitivity. Accordingly, it is preferred to consider previous measurements of the threshold of sensitivity to histamine, methacholine or acetylcholine, selecting animals having substantially equal thresholds of sensitivity to the chemical mediator, and classifying them in groups with substantially equal average threshold.

In SART stressed animals, the method of administering histamine, methacholine and the like intranasally, and the method of nasal provocation with the allergen in actively or passively sensitized animals can be employed as the method for inducing nasal secretion. There are great many patients suffering from nasal allergy induced by house dust, Japanese cedar pollen and the like. Since the method using allergen induction is similar to the total biological response system, this is a practical and logical method for evaluating antiallergic substances. In particular, the passive sensitization method is simple, can be carried out for a short term, and is preferable because the data is consistent and reproducible.

In order to induce nasal secretion in passively sensitized animals with allergen, first an antiserum to the allergen is prepared, and then nasal secretion is induced by giving the allergen intranasally, after sensitization by injecting the antiserum to test animals. The method for the preparation of antiserum and the passive sensitization method with antiserum can be similarly carried out using well known procedures. And the allergens, such as ovalbumin, DNP-ascaris and DNP-bovine serum albumin, commonly used in this field can be employed.

By using animal models with nasal mucosal hypersensitivity, the efficacy of antiallergic substances can be evaluated by the passive sensitization method with diluted antiserum, and the evaluation can be done with only a small amount of antiserum. Thus, this method is economically advantageous.

There are several methods for measuring nasal secretion, for example, visual observation and assigning a score for rhinorrhea, collecting nasal secretion by inserting an aspiration tube into the nostrils, absorbing nasal secretion utilizing filter paper and a defatted cotton thread to measure the amount of secretion by weight, measuring the amount of color change due to nasal secretion by utilizing a thread dyed with fluorescein, and the like.

When these methods are applied to small animals, the method of collecting nasal secretion by means of an aspiration tube and that of utilizing a filter paper are difficult to use because of very small nostrils and extremely small amounts of nasal secretion of these animals. And the method of making scoring rhinorrhea based on visual observation by a tester is not objective and is more qualitative than quantitative. The method of utilizing a nasal thread is preferred as the method for evaluating antiallergic substances in small animals, because it is adaptable even to a slight amount of nasal secretion, it can be used with little irritation to nasal mucosa, and it can express the amount of nasal secretion numerically and objectively. The thread for the measurement of the amount of nasal secretion can be prepared simply, for example, by suitable treatment, such as defatting a commercial cotton thread, and then dyeing the defatted thread with a fluorescein containing solution. The procedure for measuring the amount of nasal secretion is readily performed by measuring the length of fluorescein color due to nasal secretion, or measuring the weight of the defatted thread having nasal secretion absorbed thereon.

Our invention is further illustrating by means of the following non-limiting examples:

EXAMPLE 1. Method for loading SART stress

Male Hartley strain guinea pigs weighing 300 to 500 g were used. The threshold of nasal mucosal sensitivity to methacholine of these animals was previously measured with a nasal thread dyed with fluorescein, and those guinea pigs having normal sensitivity were divided into groups of 7 or 8 animals making the average of the threshold of sensitivity substantially equal in each group. To load SART stress, the guinea pigs were kept in a thermostatic box at the environmental temperature of 0° C. and 24° C. alternately for one hour period from 10:00 a.m. to 5:00 p.m., and at 0° C. from 5:00 p.m. to 10:00 a.m. the next day. This stress loading was continued for 5 days prior to sensitization.

EXAMPLE 2. Preparation of anti-ovalbumin serum

The stress-loaded guinea pigs from the previous example were sensitized intraperitoneally using 20 μg of ovalbumin and 10 mg of aluminum hydroxide (adjuvant) in 1 ml of saline 7 times every 2 weeks. After 2 weeks of the sensitization, airway sensitization was performed by ultranebulization with 3 ml of 0.1% ovalbumin in saline for 5 consecutive days. One week later, nasal provocation was performed by application of 50 μl of 1% ovalbumin in saline on both anterior nares, and antiserum was collecting from guinea pigs showing typical nasal symptoms of nasal allergy such as sneeze, nasal secretion and asthma. This anti-ovalbumin serum was preserved at −80° C.

EXAMPLE 3. Nasal provocation in passively sensitized guinea pigs

The provocation was made by application of 50 μl of 1% ovalbumin on the left anterior naris 2 days after passive sensitization by intraperitoneally injecting 2 ml of diluted anti-ovalbumin serum from the previous example (diluted ratio; ×⅛). Nasal secretion was measured The passive sensitization of SART stressed guinea pigs was affected 3 days after loading SART stress.

EXAMPLE 4. Active sensitization

Active sensitization was carried out in a manner similar to the preparation of anti-ovalbumin serum mentioned above. Namely, 1 μg ovalbumin and 5 mg of aluminum hydroxide (adjuvant) in 1 ml of saline were injected into guinea pigs intraperitoneally 6 times every 2 weeks.

EXAMPLE 5. Repeated nasal provocations with allergen to enhance nasal mucosal sensitivity Two weeks after the active sensitization with ovalbumin, 50 μl of 1% ovalbumin in saline was administered into both anterior nares to start nasal provocation with allergen. Then the nasal provocations with ovalbumin were repeated 1, 4, 7, 10 and 13 days after the first provocation.

EXAMPLE 6. Measurement of nasal secretion

Defatted cotton threads (No. 40/2) were dyed with 10% fluorescein-Na in physiological saline at one end, and were cut to a total length of 100 mm with the colored end 10 mm in length. About 15 mm of the colored end of the thread was inserted into the left anterior naris of the guinea pigs for 60 sec. The length of thread dyed with fluorescein due to nasal secretion was taken as a measure of the amount of nasal secretion. (A few threads can be used together when the amount of nasal secretion is large).

The relationship between the length of the colored portion of a thread dyed with fluorescein and the amount of nasal secretion was studied. As a result of the study, it was shown that the length of the colored portion was proportional to the increase in weight of the thread due to absorption of nasal secretion.

The efficacy of the test antiallergic substance was evaluated by using passively sensitized SART stressed guinea pigs according to the method of Examples 1, 2, 3 and 6, using 0.3 to 3.0 mg/kg/day of orally administered Ketotifen fumarate as the test substance. The amount of nasal secretion was measured by the length of the colored portion of the thread dyed with fluorescein. The test results are summarized in Table 1 below:

TABLE 1

| | Nasal secretion (mm) | Inhibition (%) |
|---|---|---|
| Normal guinea pig | 23.3 | — |
| Control | 45.0 | 0 |
| Ketotifen (0.3 mg) | 33.5 | 25.5 |
| Ketotifen (1.0 mg) | 23.9 | 46.9 |

TABLE 1-continued

| | Nasal secretion (mm) | Inhibition (%) |
|---|---|---|
| Ketotifen (3.0 mg) | 16.1 | 64.2 |

Enhanced nasal mucosal sensitivity was measured by using animals obtained by repeated nasal provocations with ovalbumin in actively sensitized guinea pigs with the allergen according to the method of Examples 4, 5 and 6. The inhibitory action for nasal secretion of Ketotifen fumarate (1.0 mg/kg/day, p.o.) was also measured using this assay system. The results observed are shown in Table 2 below:

TABLE 2

| | Nasal secretion (mm) | |
|---|---|---|
| Provocation with allergen | No test drug | Ketotifen |
| 1st | 68.8 | 68.9 |
| 2nd (1 day) | 123.3 | 54.1 |
| 3rd (4 days) | 146.6 | 73.0 |
| 4th (7 days) | 152.9 | 68.5 |
| 5th (10 days) | 187.3 | 77.3 |
| 6th (13 days) | 168.1 | 96.9 |

As indicated by the results shown in Table 1, the inhibitory action on nasal secretion of an antiallergic substance can be measured quantitatively by measuring the amount of nasal secretion using a nasal thread dyed with fluorescein in experimental animal models with nasal mucosal hypersensitivity, which are obtained by loading with SART stress. When using Ketoprofen fumarate, at doses of 0.3 to 3.0 mg/kg/day (p.o.), as a test drug, a dose-dependent inhibitory action on nasal secretion was observed.

As indicated by the results shown in Table 2, experimental animal models with nasal mucosal hypersensitivity can be obtained by repeated nasal provocations in actively sensitized animals.

Nasal sensitivity to methacholine was investigated using this assay system by administering methacholine (10 μmol) intranasally one day after each provocation with allergen. It was found that the nasal sensitivity to methacholine was enhanced by repeated nasal provocations with allergen.

Using the method of the present invention, the efficacy of antiallergic substances can be measured dose-dependently, so that the effective amount of the drug can be expressed numerically, for example, as the $ED_{50}$. However, when using normal animals, their inhibitory action on nasal secretion could not be accurately measured, and the efficacy of the antiallergic test substances could not be evaluated quantitatively.

Nasal mucosal sensitivity is often enhanced in patients suffering from nasal allergy. The method of the present invention, characterized by utilizing experimental animal models with nasal mucosal hypersensitivity, is both practical and logical, as it is carried out under experimental conditions resembling the actual diseased condition of a human patent.

The reproducibility of the method of the present invention was studied. In both approaches, loading SART stress and repeating nasal provocations with an allergen in actively sensitized animals, the experimental animal models with nasal mucosal hypersensitivity gave reproducible results.

The experimental animal models with nasal mucosal hypersensitivity by repeated nasal provocations with an allergen in actively sensitized animals have the advantage that these animals can be used in more than one series of tests. And using SART stressed animals with nasal mucosal hypersensitivity, it is possible to evaluate antiallergic substances in a simple operation, in a short time and with consistent results.

As illustrated above, the method of the present invention utilizing animal models with nasal mucosal hypersensitivity is practical, can make objective and clear evaluations and express the effective amount of drugs numerically, and is reproducible. The method of the present invention is particularly useful for measuring the efficacy of antiallergic substances in the field of the nasal allergy treatment, for example, in screening new antiallergic drugs and/or the standardization of new and already known drugs.

What is claimed is:

1. A method for evaluating the efficacy of an antiallergic substance, which comprises administering the antiallergic substance to an animal with nasal mucosal hypersensitivity, and measuring the amount of nasal secretion quantitatively by means of a nasal thread.

2. A method according to claim 1, wherein the animal with nasal mucosal hypersensitivity is an animal loaded with stress by a change of environmental rhythm prior to sensitization.

3. A method according to claim 2, wherein the animal is passively sensitized with an allergen antiserum.

4. A method according to claim 3, wherein nasal secretion is induced by nasal provocation of the animal with an allergen after sensitization.

5. A method according to claim 1, wherein the animal with nasal mucosal hypersensitivity is prepared by active sensitization with allergen and subsequent repeated nasal provocations of the animal with allergen.

6. A method according to any one of claims 1-5, wherein the animal is a guinea pig.

* * * * *